(12) United States Patent
Itoh

(10) Patent No.: US 6,986,439 B2
(45) Date of Patent: Jan. 17, 2006

(54) DISPENSING TIP POSITIONING AND STORING APPARATUS

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 140 days.

(21) Appl. No.: 10/629,871

(22) Filed: Jul. 30, 2003

(65) Prior Publication Data

US 2004/0031809 A1 Feb. 19, 2004

(30) Foreign Application Priority Data

| Jul. 31, 2002 | (JP) | ............................................. 2002-223925 |
| Jul. 15, 2003 | (JP) | ............................................. 2003-274765 |

(51) Int. Cl.
*B23Q 7/12* (2006.01)

(52) U.S. Cl. ........................................ 221/167; 221/277
(58) Field of Classification Search ................ 221/277, 221/170, 167, 168; 198/392, 396, 382
See application file for complete search history.

(56) References Cited

U.S. PATENT DOCUMENTS 5,702,028 A * 12/1997 Shirodera .................... 221/166
6,685,052 B1 * 2/2004 Nemoto et al. ............. 221/157

FOREIGN PATENT DOCUMENTS

| JP | 4-334554 | 11/1992 |
| JP | 7-833 | 1/1995 |
| JP | 2001-19182 | 1/2000 |
| JP | 2001-187629 | 7/2001 |

* cited by examiner

*Primary Examiner*—Kenneth Noland
(74) *Attorney, Agent, or Firm*—Nixon & Vanderhye P.C.

(57) ABSTRACT

A dispensing tip positioning and storing apparatus includes drum mechanisms that agitate dispensing tips, which are distributed by a tip distributor, using an agitation bar that rotates about a horizontal axis and discharge the dispensing tips while the postures of the dispensing tips are almost aligned with the horizontal axis, tip direction aligning mechanisms that align the dispensing tips, which are discharged from the drum mechanisms, in such a manner that the distal ends of the dispensing tips point downward, a conveying mechanism that sequentially conveys the dispensing tips whose directions are aligned by the tip direction aligning mechanisms, to a given position by a common conveying lane, and a tip inserting mechanism that inserts the dispensing tips, which are sequentially conveyed to the given position by the conveying mechanism, into a tip holding rack in a predetermined manner.

8 Claims, 3 Drawing Sheets

DISPENSING TIP POSITIONING AND STORING APPARATUS

CROSS-REFERENCE TO RELATED APPLICATIONS

This application is based upon and claims the benefit of priority from the prior Japanese Patent Applications No. 2002-223925, filed Jul. 31, 2002; and No. 2003-274765, filed Jul. 15, 2003, the entire contents of both of which are incorporated herein by reference.

BACKGROUND OF THE INVENTION

1. Field of the Invention

The present invention relates to a dispensing tip positioning and storing apparatus for positioning and storing a plurality of dispensing tips, which are used to dispense specimens such as blood, in a tip holding rack.

2. Description of the Related Art

Conventionally, an operator manually inserted a large number of dispensing tips (e.g., several thousand or more dispensing tips) into the tip insertion holes of a tip holding rack from a tip stocker to position and store them in the rack. This manual operation required a lot of time and high labor costs.

BRIEF SUMMARY OF THE INVENTION

An object of the present invention is to provide a dispensing tip positioning and storing apparatus that is capable of positioning and storing a large number of dispensing tips in a tip holding rack in a short time.

In order to attain the above object, a dispensing tip positioning and storing apparatus according to the present invention has the following characteristic configuration. The other characteristic configurations will be clarified in the embodiments later.

A dispensing tip positioning and storing apparatus according to the present invention, comprises a tip distributor that distributes a plurality of dispensing tips, which are carried in and are to be positioned and stored, to a plurality of processing lines, drum mechanisms provided in the processing lines, respectively, the drum mechanisms agitating the dispensing tips distributed by the tip distributor using an agitation bar that rotates about a horizontal axis and discharging the dispensing tips while postures of the dispensing tips are almost aligned with the horizontal axis, tip direction aligning mechanisms that align the dispensing tips, which are discharged from the drum mechanisms, in such a manner that distal ends of the dispensing tips point downward, a conveying mechanism that sequentially conveys the dispensing tips whose directions are aligned by the tip direction aligning mechanisms, to a given position by a common conveying lane, and a tip inserting mechanism that inserts the dispensing tips, which are sequentially conveyed to the given position by the conveying mechanism, into a tip holding rack in a predetermined manner.

DETAILED DESCRIPTION OF THE INVENTION (Embodiment)

Figure 1:
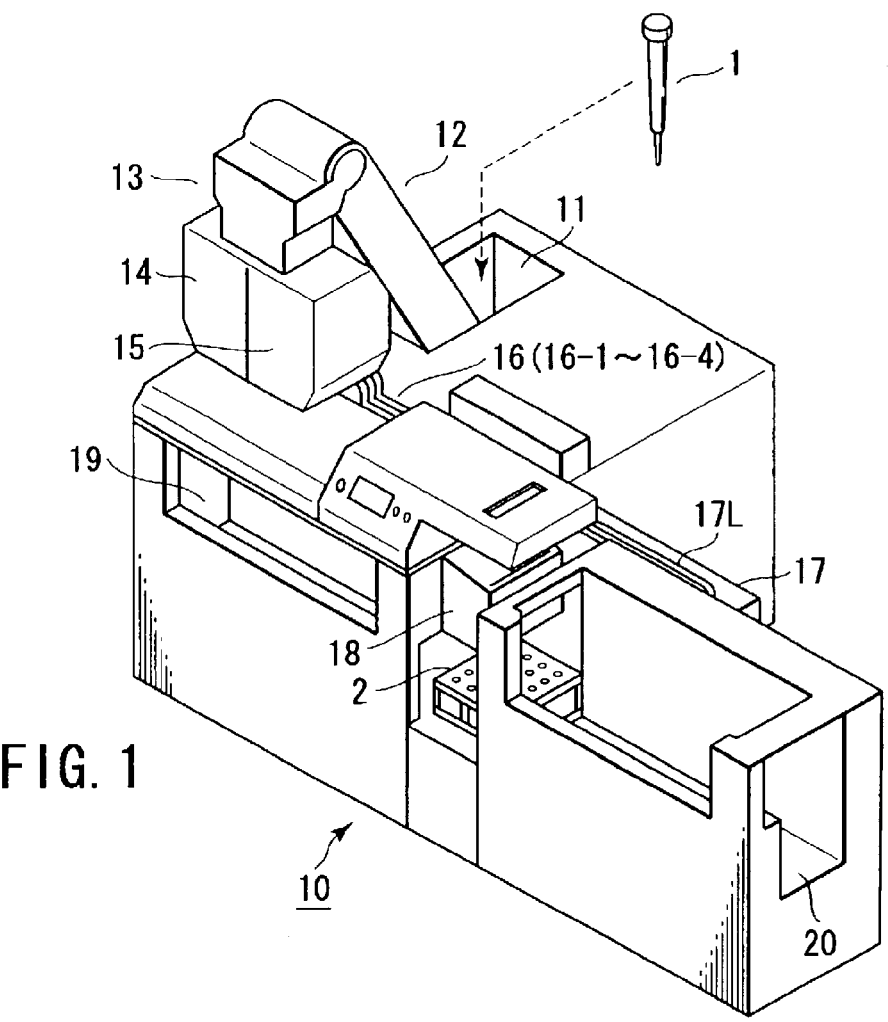
FIG. 1 is a perspective view schematically showing a dispensing tip positioning and storing apparatus according to an embodiment of the present invention.

As shown in FIG. 1, a main body 10 of a dispensing tip positioning and storing apparatus includes a tip stocker 11 for stocking a large number of dispensing tips 1, e.g., 3500 dispensing tips (one of which is shown under magnification) which are carried in from outside. A tip conveyor 12 raises the dispensing tips 1 to a tip distributor 13 provided near the top of the main body 10.

The tip distributor 13 distributes the dispensing tips 1, which are supplied from the tip conveyor 12, to a plurality of processing lines A and B (two in this embodiment). The processing lines A and B have tip agitating drum mechanisms 14 and 15, respectively. The drum mechanisms 14 and 15 are horizontally opposed to each other under the tip distributor 13. The drum mechanisms 14 and 15 agitate the dispensing tips 1, which are distributed by the tip distributor 13, align the postures of the tips in substantially a horizontal direction, and discharge them. Since the drum mechanisms 14 and 15 have substantially the same configuration, only one of the drum mechanisms, i.e., the drum mechanism 14 will be described and the description of the other drum mechanism 15 is omitted.

Figure 2:
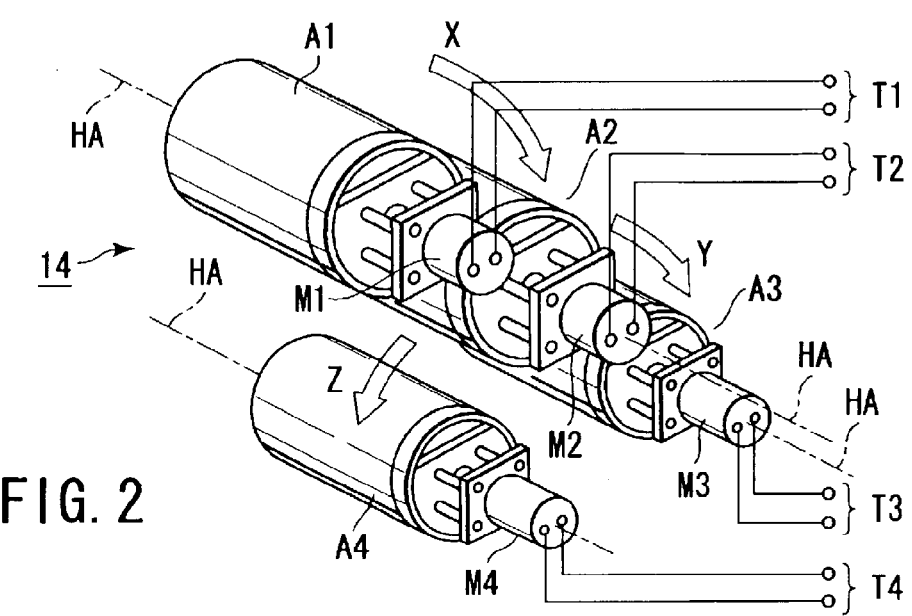
FIG. 2 is a perspective view schematically showing a drum mechanism of the dispensing tip positioning and storing apparatus according to the embodiment of the present invention.

FIG. 2 is a schematic internal view of the drum mechanism 14. Referring to FIG. 2, the drum mechanism 14 includes a first drum A1 in the top stage and a second drum A2 in the next stage or at the lower right of the first drum A1. The drum mechanism 14 further includes third and fourth drums A3 and A4 in the next stage or at the lower right and lower left of the second drum A2. In other words, basically, a plurality of drums A1 to A4 are connected to each other from the upstream side to the downstream side. The drum A2 distributes dispensing tips to the two processing lines.

The first to fourth drums A1 to A4 each have an agitation bar (described later) that rotates about a horizontal axis HA. The agitation bars of the drums A1 to A4 are rotated by their respective motors M1 to M4 that are operated by feeding from their respective terminals T1 to T4. Though not shown in FIG. 2, the first to fourth drums A1 to A4 each have a tip inlet and a tip outlet.

The first drum A1 aligns the postures or axes of the dispensing tips 1, which are supplied from the tip distributor 13, in the horizontal direction corresponding to the axis of the drum by the rotary agitation of the agitation bar. Then, the first drum A1 supplies the dispensing tips 1 to the second drum A2 little by little as indicated by arrow X.

The second drum A2 aligns the postures of the dispensing tips 1, which are supplied from the first drum A1, in substantially the horizontal direction by the same rotary agitation as that of the first drum A1. The second drum A2 distributes the dispensing tips 1 to two processing lines and supplies them to the third and fourth drums A3 and A4 little by little as indicated by arrows Y and Z.

The third and fourth drums A3 and A4 align the postures of the dispensing tips 1 in substantially the horizontal direction by the same rotary agitation as that of the first drum A1. After that, the dispensing tips 1 are discharged from the drums.

Referring back to FIG. 1, a tip direction aligning mechanism 16 (16-1 to 16-4) aligns the directions of the dispensing tips for the four processing lines, which are discharged from the third and fourth drums A3 and A4 of the drum mechanism 14 and the third and fourth drums B3 and B4 (neither of which is shown) of the drum mechanism 15, in such a manner that their distal ends point downward.

Figure 3:
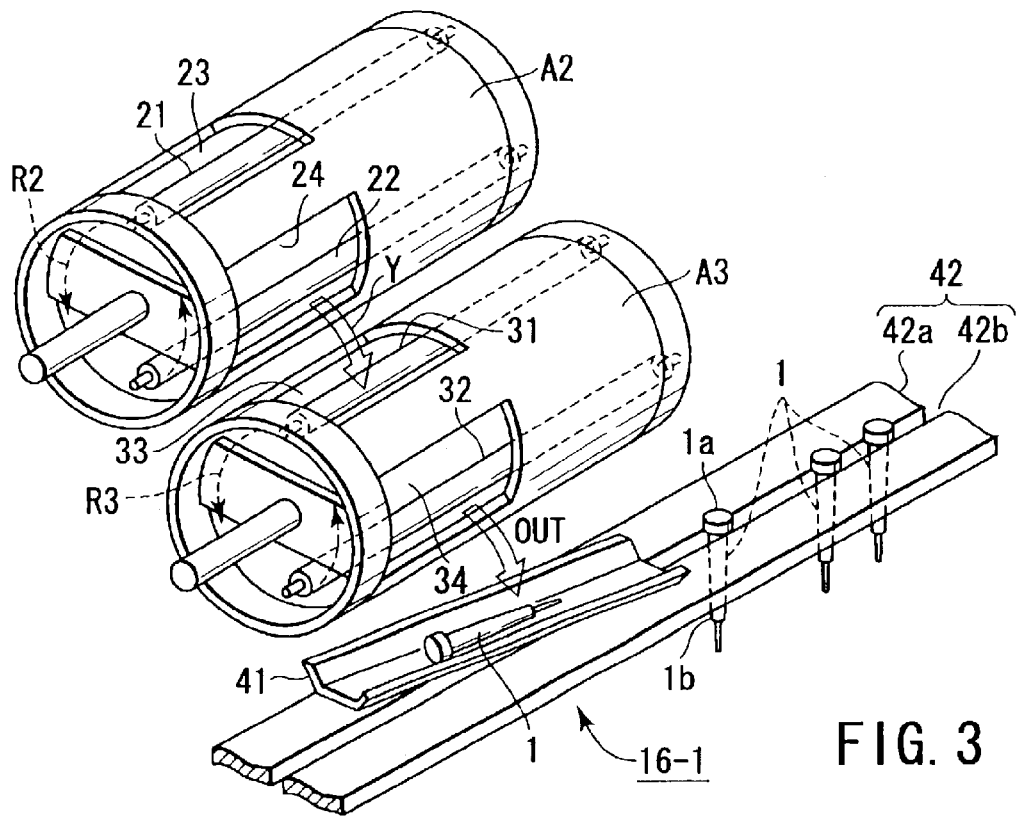
FIG. 3 is a perspective view showing part of the drum mechanism and a tip direction aligning mechanism of the dispensing tip positioning and storing apparatus according to the embodiment of the present invention.

FIG. 3 is a perspective view of the second and third drums A2 and A3 of the drum mechanism 14 and the tip direction aligning mechanism 16-1. As shown in FIG. 3, the second drum A2 has a tip inlet 23 and a tip outlet 24. Similarly, the third drum A3 has a tip inlet 33 and a tip outlet 34. The second drum A2 includes a pair of agitation bars 21 and 22 in its hollow section. Similarly, the third drum A3 includes a pair of agitation bars 31 and 32 in its hollow section.

The dispensing tips 1 (not shown) supplied into the second drum A2 are agitated by the rotation of the agitation bars 21 and 22 of the second drum A2 in the direction indicated by the broken arrow R2. This agitation allows the postures of the dispensing tips 1 to be aligned in substantially the horizontal direction corresponding to the axis of the drum A2 as described above. Some of the dispensing tips 1 whose postures are aligned in substantially the horizontal direction are raked out of the outlet 24 by the agitation bars 21 and 22 and supplied into the third drum A3 little by little as indicated by arrow Y.

The dispensing tips 1 (not shown) supplied from the second drum A2 into the third drum A3 are agitated by the rotation of the agitation bars 31 and 32 of the third drum A3 in the direction indicated by the broken arrow R3. This agitation allows the postures of the dispensing tips 1 to be aligned in substantially the horizontal direction corresponding to the axis of the drum A3 as described above. Some of the dispensing tips 1 whose postures are aligned in substantially the horizontal direction are raked out of the outlet 34 by the agitation bars 31 and 32 and supplied into the tip direction aligning mechanism 16-1 as indicated by arrow OUT.

The tip direction aligning mechanism 16-1 includes a tip receiving member 41 and a tip direction aligning lane 42. The tip receiving member 41 is shaped like a gutter and disposed with a slant under the tip outlet 34 of the third drum A3. The tip direction aligning lane 42 is located under the tip receiving member 41 and has a slit 42b along the centerline of a band-like member 42a. The slit 42b has a width to prevent only a head portion of each of the dispensing tips 1 from passing through the slit.

Thus, the dispensing tips 1 discharged from the third drum A3 slide down on the tip receiving member 41 to the tip direction aligning lane 42. The dispensing tips 1 are each put on the lane 42 such that its portion 1b other than the head portion 1a is projected downward from the slit 42b. In other words, the tips 1 hang from the lane 42 with their distal ends 1b downward. Whether the head portions of the dispensing tips 1 sliding down on the tip receiving member 41 point upward or downward, they uniformly hang from the tip direction aligning lane 42 with their distal ends downward. Therefore, the dispensing tips 1 are aligned.

Referring back to FIG. 1, a conveying mechanism 17 sequentially conveys the dispensing tips 1, which are carried by the four tip direction aligning mechanisms 16-1 to 16-4, to a dispensing tip inserting mechanism (tip shooter) 18 through a common tip conveying lane 17L.

Figure 4:
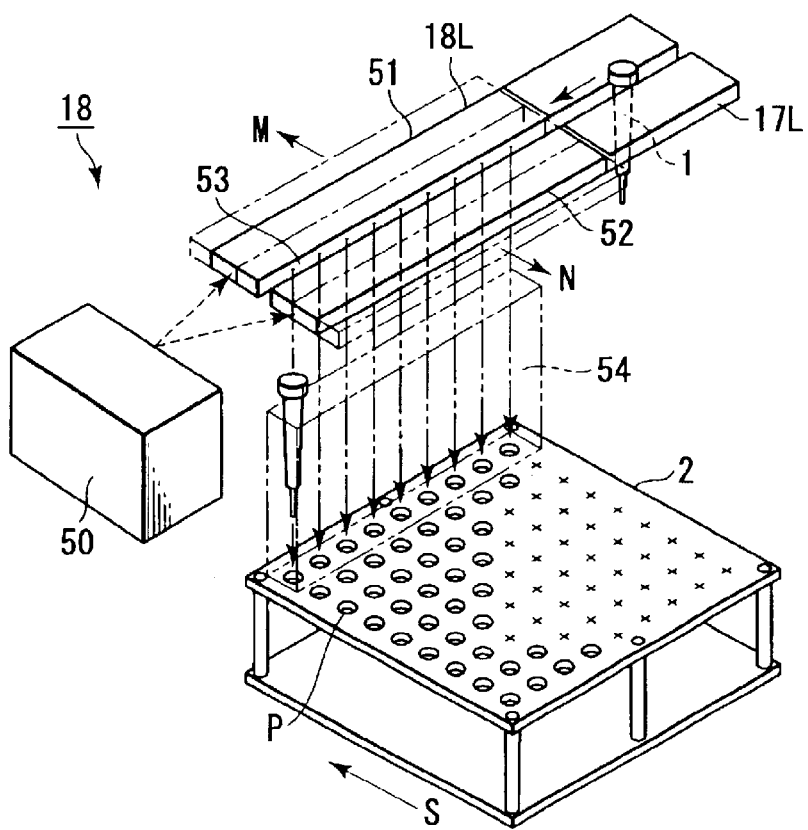
FIG. 4 is a perspective view showing a dispensing tip inserting mechanism of the dispensing tip positioning and storing apparatus according to the embodiment of the present invention.

FIG. 4 is a perspective view of the dispensing tip inserting mechanism 18. As shown in FIG. 4, the tip inserting mechanism 18 includes a tip holding lane 18L having a given length. The tip holding lane 18L communicates with the tip conveying lane 17L and takes the same shape as that of the lane 17L. The tip holding lane 18L is made up of a pair of band-like lane members 51 and 52, and these lane members 51 and 52 can be opened to both sides as indicated by arrows M and N by a driving control mechanism 50. A tip holding rack 2 is set under the tip holding lane 18L in a position-adjustable manner as indicated by arrow S. A guide section 54, which is indicated by a double dot and dash line, is provided to perform communication between a slit 53 formed along the centerline of the tip holding lane 18L and one line of tip inserting holes P of the tip holding rack 2. It is preferable that the guide section 54 is slightly inclined like a slide. It is also preferable that the guide section 54 has separate inserting passages (e.g., gutters) to bring the dispensing tips 1 held by the tip holding lane 18L and the tip inserting holes P of the tip holding rack 2 into one-to-one correspondence with each other.

Thus, the dispensing tips 1 conveyed in sequence to the tip storing position by the tip conveying lane 17 are divided into groups each having a plurality of tips (nine tips in this embodiment) on the tip holding lane 18L. When the lane members 51 and 52 of the tip holding lane 18L are opened to both sides as indicated by arrows M and N by the driving control mechanism 50, the holding of the head portions 1a of the grouped dispensing tips 1 is released. Thus, these dispensing tips are guided by the guide section 54 and inserted together into the tip inserting holes P of the tip holding rack 2 set in a given position in advance. The tip holding rack 2 moves in the direction of arrow S by one row of tip inserting holes and prepares for the next tip insertion. After that, the same operation is repeated to hold the dispensing tips 1 in the tip holding rack in a predetermined manner.

Referring back to FIG. 1, a rack carry-in mechanism 19 carries an empty tip holding rack 2 into the main body 10 and sets the dispensing tips 1 in a storable position. A rack carry-out mechanism 20 carries a tip holding rack 2 whose tip inserting holes P are filled with the dispensing tips 1 outside the main body 10.

Figure 5:
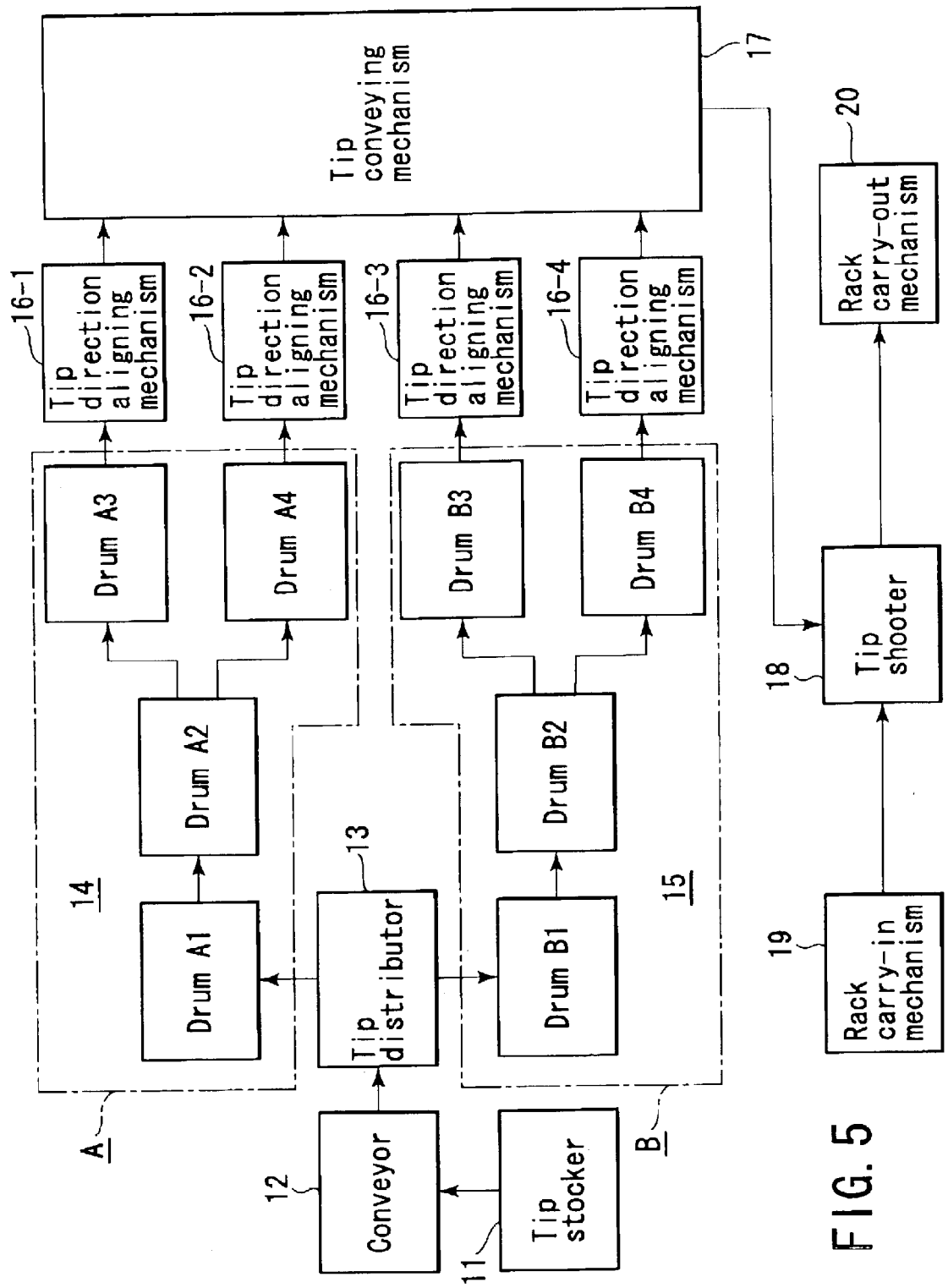
FIG. 5 is block diagram showing a function of the dispensing tip positioning and storing apparatus according to the embodiment of the present invention.

FIG. 5 is a block diagram showing a function of the dispensing tip positioning and storing apparatus according to the present embodiment. An operation of the apparatus will now be described with reference to FIG. 5. The dispensing tips 1 stocked in the tip stocker 11 are supplied to the tip distributor 13 by the tip conveyor 12. The tip distributor 13 distributes the dispensing tips 1 to two processing lines A and B.

The dispensing tips 1 distributed to the processing lines A and B are aligned by the rotary agitation of the drum mechanisms 14 and 15 provided in their respective processing lines A and B in such a manner that their postures or axes coincide with the axes of the drums of each of the drum mechanisms. The dispensing tips 1 whose postures are aligned are discharged from the drum mechanisms 14 and 15, and the directions of the tips 1 are aligned by the four tip direction aligning mechanisms 16-1 to 16-4 such that their distal ends point downward. These dispensing tips 1 are moved to the conveying mechanism 17. The dispensing tips 1 moved to the conveying mechanism 17 are sequentially conveyed in line to a predetermined position through the common conveying lane 17L. The conveyed dispensing tips 1 are divided into groups each having a plurality of tips and held by the tip holding lane 18L of the tip inserting mechanism 18. Then, when the lane members 51 and 52 of the tip holding lane 18L are opened to both sides, the grouped dispensing tips held by the tip holding lane 18L are inserted into their respective inserting holes P of an empty tip holding rack 2 that is previously carried in by the rack carry-in mechanism 19 and is set in a given position. This operation is repeated to quickly insert the dispensing tips 1 in sequence into the tip inserting holes P. Consequently, the dispensing tips 1 are stocked in the tip holding rack 2 in a predetermined manner. The tip inserting holes P are filled with the dispensing tips 1 and the tip holding rack 2 including a given number of dispensing tips is carried outside the dispensing tip positioning and storing apparatus by the rack carry-out mechanism 20.

(Features of the Embodiment)

[1] A dispensing tip positioning and storing apparatus according to an embodiment of the present invention, comprises:

a tip distributor 13 that distributes a plurality of dispensing tips 1, which are carried in and are to be positioned and stored, to a plurality of processing lines A and B;

drum mechanisms 14 and 15 provided in the processing lines A and B, respectively, the drum mechanisms agitating the dispensing tips 1 distributed by the tip distributor 13 using an agitation bar (21, 22, 31, 32, . . . ) that rotates about a horizontal axis HA and discharging the dispensing tips 1 while the postures of the dispensing tips 1 are almost aligned with the horizontal axis HA;

tip direction aligning mechanisms 16-1 to 16-4 that align the dispensing tips 1, which are discharged from the drum mechanisms 14 and 15, in such a manner that the distal ends of the dispensing tips point downward;

a conveying mechanism 17 that sequentially conveys the dispensing tips 1 whose directions are aligned by the tip direction aligning mechanisms 16-1 to 16-4, to a given position by a common conveying lane 17L; and a tip inserting mechanism 18 that inserts the dispensing tips 1, which are sequentially conveyed to the given position by the conveying mechanism 17, into a tip holding rack 2 in a predetermined manner.

In the above dispensing tip positioning and storing apparatus, the dispensing tips 1 carried in from outside are distributed to the processing lines A and B by the tip distributor 13. The postures of the dispensing tips 1 are almost aligned with the axes of the drums in the drum mechanisms 14 and 15 by the agitating operation of the drum mechanisms 14 and 15. The directions of the posture-aligned dispensing tips 1 are aligned by the tip direction aligning mechanisms 16-1 to 16-4 in such a manner that their distal ends point downward. After that, the dispensing tips 1 are moved in line and conveyed in sequence to a given position through the common conveying lane 17L. In this given position, the dispensing tips 1 are inserted into the tip inserting holes P of the tip holding rack 2 by the tip inserting mechanism 18 and stored in a predetermined manner.

[2] In the dispensing tip positioning and storing apparatus described in the above item [1], the drum mechanisms 14 and 15 are provided under the tip distributor 13.

In the above dispensing tip positioning and storing apparatus, the dispensing tips 1 distributed by the tip distributor 13 are naturally dropped into the drum mechanisms 14 and 15 under their own weight without providing any special conveying means.

[3] In the dispensing tip positioning and storing apparatus described in one of the above items [1] and [2], the drum mechanism 14 includes a plurality of drums A1 to A4 which are connected from the upstream side to the downstream side and the drum mechanism 15 includes a plurality of drums B1 to B4 which are connected to each other from the upstream side to the downstream side, and the drums A1 to A4 and B1 to B4 agitate the dispensing tips 1 supplied from above, align the postures of the dispensing tips 1 in substantially a horizontal direction, and discharge the dispensing tips 1 downward.

In the above dispensing tip positioning and storing apparatus, the drums A1 to A4 and B1 to B4 are connected to each other from the upstream side to the downstream side. Therefore, even though the directions of all the dispensing tips 1 are not aligned in the first (uppermost) drum A1 or B1, they are done in the second drum A2 or B2 or one of the subsequent drums.

[4] In the dispensing tip positioning and storing apparatus described in the above item [3], each of the drum mechanisms 14 and 15 includes at least one drum (A2, B2, etc.) having a function of further distributing the dispensing tips 1, which flow through the processing line of the drum mechanism, to a plurality of processing lines.

In the above dispensing tip positioning and storing apparatus, since the dispensing tips 1 flowing through one processing line are further distributed to a plurality of processing lines, their subsequent agitating operation is sufficiently performed by the drums. Therefore, even though the number of drums is relatively small, the directions of the dispensing tips 1 can efficiently be aligned.

[5] In the dispensing tip positioning and storing apparatus described in the above item [1], each of the tip direction aligning mechanisms 16-1 to 16-4 includes:

a gutter-shaped tip receiving member 41 that is inclined under a tip outlet of each of the drum mechanisms; and a tip direction aligning lane 42 provided under the tip receiving member 41 and having a slit 42b formed along the centerline of a band-shaped member 42, the slit 42b having a width to prevent only the head portion of each of the dispensing tips 1 from passing through the slit.

In the above dispensing tip positioning and storing apparatus, the directions of the dispensing tips 1 are aligned such that their distal ends 1b always point downward by the tip direction aligning lane 42 regardless of whether the head portions 1a of the dispensing tips 1 sliding on the tip receiving member 41.

[6] In the dispensing tip positioning and storing apparatus described in the above item [1], the tip inserting mechanism 18 is a tip shooter that shoots the dispensing tips 1 with their distal ends downward, which are sequentially conveyed to a given position by the conveying mechanism 17, into the tip inserting holes P of the tip holding rack 2.

In the above dispensing tip positioning and storing apparatus, the dispensing tips 1 can sufficiently be inserted into the tip inserting holes P of the tip holding rack 2.

What is claimed is:

1. A dispensing tip positioning and storing apparatus comprising:

a tip distributor that distributes a plurality of dispensing tips, which are carried in and are to be positioned and stored, to a plurality of processing lines;

drum mechanisms provided in the processing lines, respectively, the drum mechanisms agitating the dispensing tips distributed by the tip distributor using an agitation bar that rotates about a horizontal axis and discharging the dispensing tips while postures of the dispensing tips are almost aligned with the horizontal axis;

tip direction aligning mechanisms that align the dispensing tips, which are discharged from the drum mechanisms, in such a manner that distal ends of the dispensing tips point downward;

a conveying mechanism that sequentially conveys the dispensing tips whose directions are aligned by the tip direction aligning mechanisms, to a given position by a common conveying lane; and a tip inserting mechanism that inserts the dispensing tips, which are sequentially conveyed to the given position by the conveying mechanism, into a tip holding rack in a predetermined manner.

2. The dispensing tip positioning and storing apparatus according to claim 1, wherein the drum mechanisms are provided under the tip distributor.

3. The dispensing tip positioning and storing apparatus according to claim 1, wherein each of the drum mechanisms includes a plurality of drums which are connected to each other from an upstream side to a downstream side, and the drums agitate the dispensing tips supplied from above, align the postures of the dispensing tips in substantially a horizontal direction, and discharge the dispensing tips downward.

4. The dispensing tip positioning and storing apparatus according to claim 2, wherein each of the drum mechanisms includes a plurality of drums which are connected to each other from an upstream side to a downstream side, and the drums agitate the dispensing tips supplied from above, align the postures of the dispensing tips in substantially a horizontal direction, and discharge the dispensing tips downward.

5. The dispensing tip positioning and storing apparatus according to claim 3, wherein each of the drum mechanisms includes at least one drum having a function of further distributing the dispensing tips, which flow through a processing line of the drum mechanism, to a plurality of processing lines.

6. The dispensing tip positioning and storing apparatus according to claim 4, wherein each of the drum mechanisms includes at least one drum having a function of further distributing the dispensing tips, which flow through a processing line of the drum mechanism, to a plurality of processing lines.

7. The dispensing tip positioning and storing apparatus according to claim 1, wherein each of the tip direction aligning mechanisms includes:

a gutter-shaped tip receiving member that is inclined under a tip outlet of each of the drum mechanisms; and a tip direction aligning lane provided under the tip receiving member and having a slit formed along a centerline of a band-shaped member, the slit having a width as to prevent only a head portion of each of the dispensing tips from passing through the slit.

8. The dispensing tip positioning and storing apparatus according to claim 1, wherein the tip inserting mechanism is a tip shooter that shoots the dispensing tips with distal ends of the dispensing tips downward, which are sequentially conveyed to the given position by the conveying mechanism, into the tip inserting holes of the tip holding rack.

* * * * *